US008809589B2

(12) United States Patent
Gore et al.

(10) Patent No.: US 8,809,589 B2
(45) Date of Patent: Aug. 19, 2014

(54) PROCESS FOR THE PREPARATION OF ENANTIOMERICALLY PURE AMINES

(71) Applicant: Generics [UK] Limited, Hertfordshire (GB)

(72) Inventors: Vinayak Govind Gore, Maharashtra (IN); Bindu Manojkumar, Maharashtra (IN); Sandeep Sonawane, Maharashtra (IN); Dattatrey Kokane, Maharashtra (IN); Sinderpal Tank, Maharashtra (IN)

(73) Assignee: Generics [UK] Limited, Hertfordshire (GB)

( * ) Notice: Subject to any disclaimer, the term of this patent is extended or adjusted under 35 U.S.C. 154(b) by 0 days.

(21) Appl. No.: 13/944,956

(22) Filed: Jul. 18, 2013

(65) Prior Publication Data
US 2013/0303741 A1   Nov. 14, 2013

Related U.S. Application Data

(62) Division of application No. 12/992,451, filed as application No. PCT/GB2009/050608 on Jun. 2, 2009, now Pat. No. 8,569,545.

(30) Foreign Application Priority Data

Jun. 2, 2008 (IN) .............................. 973/KOL/2008

(51) Int. Cl.
C07C 211/42 (2006.01)
(52) U.S. Cl.
USPC ........................................................ 564/428
(58) Field of Classification Search
USPC ........................................................ 564/428
See application file for complete search history.

(56) References Cited

U.S. PATENT DOCUMENTS

| 3,198,834 | A |   | 8/1965  | Beregi et al.            |
|-----------|---|---|---------|--------------------------|
| 3,728,388 | A |   | 4/1973  | Schulenberg              |
| 3,855,227 | A |   | 12/1974 | Den Hollander et al.     |
| 3,912,761 | A |   | 10/1975 | Den Hollander et al.     |
| 3,928,621 | A |   | 12/1975 | Boris                    |
| 5,457,133 | A |   | 10/1995 | Youdim et al.            |
| 5,532,415 | A |   | 7/1996  | Youdim et al.            |
| 5,994,408 | A |   | 11/1999 | Cohen et al.             |
| 8,569,545 | B2| * | 10/2013 | Gore et al. ....... 564/428|
| 2003/0065038 | A1 | | 4/2003 | Youdim et al.            |
| 2006/0199974 | A1 | | 9/2006 | Boulton et al.           |
| 2007/0093495 | A1 | | 4/2007 | Ruggero et al.           |
| 2007/0100001 | A1 | | 5/2007 | Youdim et al.            |

FOREIGN PATENT DOCUMENTS

| CA | 2 684 977   | 11/2008 |
| CN | 1062900     | 7/1992  |
| CN | 101062897   | 10/2007 |
| EP | 0235590     | 9/1987  |
| EP | 1 987 816   | 11/2008 |
| JP | S43-16970   | 7/1968  |
| JP | S52-83938   | 7/1977  |
| JP | S59-67249 A | 1/1984  |
| JP | S62-185058  | 9/1987  |
| JP | H01-500665  | 9/1989  |
| JP | H02-19348   | 12/1989 |
| JP | H0-3294248 A| 7/1991  |
| JP | H04-211079  | 8/1991  |
| JP | H0-9505806  | 4/1995  |
| JP | H08-143516  | 4/1996  |
| JP | H0-9510188 A| 11/1999 |
| JP | 2008531546 A| 9/2006  |
| JP | 2009521402 A| 6/2009  |
| WO | WO 95/11016 | 4/1995  |
| WO | WO 96/37199 | 11/1996 |
| WO | WO 02/068376| 9/2002  |
| WO | WO 2007/061717 | 5/2007 |
| WO | WO 2008/076348 | 6/2008 |
| WO | WO 2009/147432 | 12/2009|
| WO | WO 2010/013048 | 2/2010 |

OTHER PUBLICATIONS

Reddy et al, "Dirhodium Tetracarboxylates Derived from Adamantylglycine as Chiral Catalysts for Enantioselective C-H Aminations", Supporting Info, Organic letters, 2006, vol. 8(2), pp. 5013-5016.
Clayden et al., Organic Chemistry, Oxford University Press, 2001., p. 1291.
Aldrich Catalogue 1996-1997, p. 871.
Biochemistry, vol. 19, 1980, pp. 2133-2139.
J. March, Advanced Organic Chemistry, 3$^{rd}$ Ed., 1985, p. 312.
Nucleosides and nucleotides, 2002, vol. 21, pp. 45-54.
Organic Letters, vol. 8, 2006, pp. 5013-5016.

(Continued)

*Primary Examiner* — Rei-tsang Shiao
(74) *Attorney, Agent, or Firm* — Fulbright & Jaworski LLP; Scott D. Rothenberger

(57) ABSTRACT

The present invention relates to an improved process for the preparation of (R)-1-aminoindan (2), rasagiline (1) and pharmaceutically acceptable salts of rasagiline.

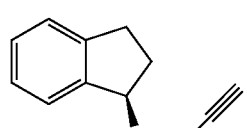

(1)

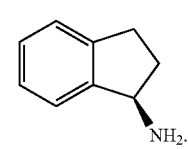

(2)

14 Claims, No Drawings

(56) References Cited

OTHER PUBLICATIONS

Synthesis, 2001, pp. 478-482.
Topics in Current Chemistry, 1998, vol. 198, pp. 163-208.
Wikipedia extract re "Mesylate", 2009.
Wikipedia extract re "Nonaflate", 2009.
Wikipedia extract re "Trifluoromethanesulfonate", 2009.
Wikipedia extract re "Tosyl", 2009.
Organic Syntheses, coll. vol. 5, p. 932 (1973); vol. 49, p. 93 (1969).
International Search Report PCT/GB2009/050608 dated Jul. 28, 2009 (3 pgs.).
International Preliminary Report on Patentability from related PCT application PCT/GB2009/050608 dated Dec. 16, 2010, 8 pages.

\* cited by examiner

PROCESS FOR THE PREPARATION OF ENANTIOMERICALLY PURE AMINES

CROSS-REFERENCE TO RELATED APPLICATION(s)

This application is a Divisional of 12/992,451 filed Nov. 12, 2010, which is a Section 371 National Stage Application of International No. PCT/GB2009/050608, filed 2 Jun. 2009 and published as WO 2009/147430 A1 on 10 Dec. 2009, which claims priority from the IN Patent Application No. 973/KOL/2008, filed 2 Jun. 2008, the contents of which are incorporated herein in their entirety for all purposes.

FIELD OF THE INVENTION

The present invention relates to an improved process for the preparation of (R)-1-aminoindan (2), rasagiline (1) and pharmaceutically acceptable salts of rasagiline.

BACKGROUND OF THE INVENTION

Rasagiline, represented by structural formula (1) and chemically named 1-(R)-(2-propynylamino)indan, is a selective and potent irreversible monoamine oxidase type B (MAO-B) inhibitor. It is currently marketed, as the mesylate salt, for the treatment of Parkinson's Disease (PD), both as monotherapy and as adjunct therapy to levodopa. Rasagiline (1) may also be useful for the treatment of dementia, Alzheimer's Disease, depression, hyperactive syndrome, stroke, brain ischemia, neurotrauma, schizophrenia and multiple sclerosis.

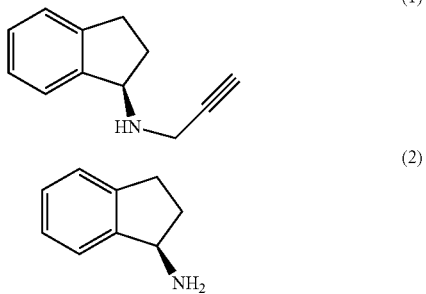

Rasagiline (1) was first described in U.S. Pat. No. 5,457,133, in which the method of its preparation is a single step process comprising reacting (R)-1-aminoindan (2) with propargyl chloride. The reaction is carried out in acetonitrile with potassium carbonate at a temperature of 60° C. for 16 hours.

The preparation of (R)-1-aminoindan (2) is disclosed in an article by Lawson and Rao in *Biochemistry*, vol. 19, pages 2133-2139, 1980, in which racemic 1-aminoindan is resolved via fractional crystallization of its diastereomeric salt with L-malic acid in ethanol. However, the purification procedures disclosed are difficult and time consuming and do not afford very pure product.

The preparation of (R)-1-aminoindan (2) is also disclosed in EP 235590, in which racemic 1-aminoindan is resolved via fractional crystallization of its diastereomeric salt with the expensive resolving agent D-N-acetyl-3,4-dimethoxyphenylalanine in methanol. However, again the purification procedures disclosed are difficult, time consuming and do not afford very pure product.

U.S. Pat. No. 5,994,408 discloses a method for the preparation of (R)-1-aminoindan (2) via resolution of N-benzyl-1-aminoindan using (S)-mandelic acid. However, this process is long and involves multiple protection/deprotection steps and, again, the purification procedures disclosed are difficult, time consuming and do not afford very pure product.

Another process for the preparation of rasagiline (1) via (R)-1-aminoindan (2), disclosed in patent application WO 02/068376, involves the preparation of N-benzyl-1-aminoindan from indanone or 1-chloroindan and benzylamine. Resolution of N-benzyl-1-aminoindan using L-tartaric acid and catalytic hydrogenolysis to remove the benzyl group affords (R)-1-aminoindan (2), which is further converted to rasagiline (1) by reaction with propargyl chloride. This process suffers from the drawback of having many steps including protection and deprotection, and the overall yield for the preparation of (R)-1-aminoindan (2) was reported to be a very low 19%.

An alternative process for the preparation of rasagiline (1), disclosed in patent application WO 95/11016, involves reaction of racemic 1-aminoindan with propargyl benzenesulfonate in the presence of 15% aqueous NaOH in toluene to form racemic rasagiline. The racemic rasagiline is then resolved to form rasagiline (1) via fractional crystallization of its diastereomeric salt with L-tartaric acid. However, the reported process is low yielding and affords an impure product.

US 2006/0199974 discloses a process which involves asymmetric reduction of indanone to (S)-indanol followed by conversion to the corresponding tosylate which undergoes coupling with propargylamine to afford rasagiline (1). The overall yield was reported as 66%. This process is economically and commercially not suitable as an expensive catalyst is used for the asymmetric reduction.

Therefore the prior art processes for the preparation of rasagiline (1) can be classed into three main categories: firstly, reaction of (R)-1-aminoindan (2) with a propargyl alkylating agent; secondly, reaction of racemic 1-aminoindan with a propargyl alkylating agent followed by resolution of the racemic rasagiline formed; and thirdly, longer chemical syntheses involving resolution or stereospecific synthesis of different intermediates.

For the commercial preparation of rasagiline (1) and its pharmaceutically acceptable salts, the first approach is the most efficient in principle. The second and third approaches suffer from the disadvantages of using expensive reagents; being multi-step, long processes; being low yielding; and/or producing impure products which require substantial purification. However, although the first approach is the most attractive in principle, the reported processes following this general approach are not very efficient and do not give a high yielding, economically and commercially viable process for generating the required enantiomerically pure (R)-1-aminoindan (2).

In view of the above disadvantages associated with the prior art, there is a need for an improved process for the preparation of enantiomerically pure (R)-1-aminoindan (2) which does not involve multiple steps, uses relatively inexpensive reagents, eliminates the need for cumbersome purification techniques, is economical and high yielding, and which provides (R)-1-aminoindan (2) with a high degree of purity.

As the commercial production of rasagiline (1) and rasagiline mesylate are of great importance and in view of the above disadvantages associated with the prior art, there is a real need for alternative and improved processes for the preparation of rasagiline (1) and rasagiline mesylate which do not involve multiple steps and further eliminate the need for cumbersome purification techniques. The alternative processes must be economical and high yielding and provide rasagiline (1) and rasagiline mesylate with a high degree of chemical and optical purity.

SUMMARY OF THE INVENTION

The difficulties encountered in the prior art when preparing enantiomerically pure (R)-1-aminoindan (2) and rasagiline (1) have been successfully overcome in the present invention.

The term "(R)-1-aminoindan" as used herein throughout the description and claims means (R)-1-aminoindan and/or any salt, solvate or polymorphic form thereof, unless otherwise specified. The term "rasagiline" as used herein throughout the description and claims means rasagiline and/or any salt, solvate or polymorphic form thereof, unless otherwise specified.

Salts of (R)-1-aminoindan and rasagiline include acid addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulfuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulfonic acids (for example, methanesulfonic, trifluoromethanesulfonic, ethanesulfonic, 2-hydroxyethanesulfonic, benzenesulfonic, toluene-p-sulfonic, naphthalene-2-sulfonic or camphorsulfonic acid) or amino acids (for example, ornithinic, glutamic or aspartic acid). A preferred salt of rasagiline is the methanesulfonic acid addition salt, also called rasagiline mesylate.

For the purposes of the present invention, the 1-aminoindan, rasagiline or rasagiline mesylate is "enantiomerically pure", if it comprises 95% or more of only one enantiomer, preferably 98% or more, preferably 99% or more, preferably 99.5% or more, preferably 99.9% or more, for example as measured by chiral HPLC.

For the purposes of the present invention, the 1-aminoindan, rasagiline or rasagiline mesylate is "racemic", if it comprises its enantiomers in a ratio of 70:30 to 30:70, for example as measured by chiral HPLC.

For the purposes of the present invention, the 1-aminoindan, rasagiline or rasagiline mesylate is "substantially free" of chemical impurities, if it comprises less than 3% impurity, preferably less than 2%, preferably less than 1%, preferably less than 0.5%, preferably less than 0.1%, for example as measured by HPLC.

The present invention provides an efficient and economical synthesis of (R)-1-aminoindan (2) which can readily be converted to rasagiline (1) and its pharmaceutically acceptable salts, such as the mesylate salt. The process of the present invention is high yielding and affords the products with very high chemical and optical purity on a commercial scale, without the need for cumbersome purification techniques.

Accordingly, a first aspect according to the present invention provides a process for the preparation of enantiomerically pure (R)-1-aminoindan (2) comprising the formation of a diastereomeric salt of 1-aminoindan with 2,3,4,6-di-O-isopropylidene-2-keto-L -gulonic acid. Preferably the 1-aminoindan used is racemic.

The term "2,3,4,6-di-O-isopropylidene-2-keto-L-gulonic acid" as used herein throughout the description and claims includes 2,3,4,6-di-O-isopropylidene-2-keto-L-gulonic acid and its hydrates, such as 2,3,4,6-di-O-isopropylidene-2-keto-L-gulonic acid monohydrate.

Preferably, the salt formation takes place in an organic solvent or a mixture of an organic solvent and water. The organic solvent is preferably a $C_1$-$C_6$ alcohol, preferably selected from the group comprising methanol, ethanol, n-propanol, isopropanol, n-butanol, isobutanol, tert-butanol and mixtures thereof. Most preferably, the organic solvent is methanol, optionally mixed with water.

Most preferably, the mixture of an organic solvent and water is a mixture of methanol and water. Preferably, if an organic solvent and water mixture is used, the ratio of the organic solvent to water is between from about 1:0.1 to 1:2, more preferably from about 1:0.5 to 1:1.5, and most preferably about 1:0.5.

If so desired, the diastereomeric salt formed may be recrystallised, preferably from an organic solvent or water or a mixture thereof. The organic solvent is a preferably a $C_1$-$C_6$ alcohol, preferably selected from the group comprising methanol, ethanol, n-propanol, isopropanol, n-butanol, isobutanol, tert-butanol and mixtures thereof. Most preferably, the organic solvent is methanol, optionally mixed with water.

Preferably, the diastereomeric salt formed is recrystallised from a mixture of methanol and water. Preferably, the methanol to water ratio is between from about 1:0.1 to 1:2, more preferably from about 1:0.5 to 1:1.5, and most preferably between about 1:0.75 to 1:1.5.

Preferably, the (R)-1-aminoindan (2) formed is converted to rasagiline (1) or a pharmaceutically acceptable salt thereof. Most preferably, the pharmaceutically acceptable salt of rasagiline (1) is a mesylate salt.

Preferably, the (R)-1-aminoindan (2), rasagiline (1) or rasagiline salt are obtained in a yield of 70% or more, preferably 80% or more, preferably 90% or more, preferably 95% or more.

Preferably, the (R)-1-aminoindan (2), rasagiline (1) or rasagiline salt are obtained on a commercial scale, preferably in batches of 1 kg or more, 10 kg or more, 100 kg or more, 500 kg or more, or 1000 kg or more.

Preferably, the (R)-1-aminoindan (2), rasagiline (1) or rasagiline salt obtained are enantiomerically pure, i.e. preferably they comprise 95% or more of only one enantiomer, preferably 98% or more, preferably 99% or more, preferably 99.5 % or more, preferably 99.9 % or more, for example as measured by chiral HPLC.

Preferably, the (R)-1-aminoindan (2), rasagiline (1) or rasagiline salt obtained are substantially free of chemical impurities, i.e. preferably they comprise less than 3% impurity, preferably less than 2%, preferably less than 1%, preferably less than 0.5%, preferably less than 0.1%, for example as measured by HPLC.

Preferably this optical and chemical purity is achieved without the use of chromatography.

A second aspect of the present invention provides rasagiline (1) or a pharmaceutically acceptable salt thereof, such as rasagiline mesylate, when prepared by a process according to the first aspect of the present invention.

A third aspect of the present invention provides enantiomerically pure rasagiline (1) or an enantiomerically pure pharmaceutically acceptable salt of rasagiline (1), such as enantiomerically pure rasagiline mesylate, when prepared by a process according to the first aspect of the present invention.

A fourth aspect of the present invention provides enantiomerically pure rasagiline (1) or an enantiomerically pure pharmaceutically acceptable salt of rasagiline (1), such as enantiomerically pure rasagiline mesylate.

A fifth aspect of the present invention provides rasagiline (1) substantially free of chemical impurities or a pharmaceutically acceptable salt of rasagiline (1), such as rasagiline mesylate, substantially free of chemical impurities.

The pharmaceutically acceptable salts of rasagiline (1) according to the second, third, fourth or fifth aspect of the present invention include acid addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulfuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulfonic acids (for example, methanesulfonic, trifluoromethanesulfonic, ethanesulfonic, 2-hydroxyethanesulfonic, benzenesulfonic, toluene-p-sulfonic, naphthalene-2-sulfonic or camphorsulfonic acid) or amino acids (for example, ornithinic, glutamic or aspartic acid). A preferred pharmaceutically acceptable salt of rasagiline (1) is the methanesulfonic acid addition salt, also called rasagiline mesylate.

Preferably the rasagiline (1) and the pharmaceutically acceptable salt thereof, such as rasagiline mesylate, according to the second, third, fourth or fifth aspect of the present invention is suitable for treating or preventing Parkinson's Disease (PD) (including as monotherapy or as adjunct therapy to levodopa), dementia, Alzheimer's Disease, depression, hyperactive syndrome, stroke, brain ischemia, neurotrauma, schizophrenia or multiple sclerosis.

A sixth aspect of the present invention provides a pharmaceutical composition comprising the rasagiline (1) or the pharmaceutically acceptable salt thereof, such as rasagiline mesylate, according to the second, third, fourth or fifth aspect of the present invention. Preferably the pharmaceutical composition is suitable for treating or preventing Parkinson's Disease (PD) (including as monotherapy or as adjunct therapy to levodopa), dementia, Alzheimer's Disease, depression, hyperactive syndrome, stroke, brain ischemia, neurotrauma, schizophrenia or multiple sclerosis.

A seventh aspect of the present invention provides a method of treating or preventing Parkinson's Disease (PD) (including as monotherapy or as adjunct therapy to levodopa), dementia, Alzheimer's Disease, depression, hyperactive syndrome, stroke, brain ischemia, neurotrauma, schizophrenia or multiple sclerosis, comprising administering to a patient in need thereof a therapeutically or prophylactically effective amount of the rasagiline (1) or the pharmaceutically acceptable salt thereof, such as rasagiline mesylate, according to the second, third, fourth or fifth aspect of the present invention, or a therapeutically or prophylactically effective amount of the pharmaceutical composition according to the sixth aspect of the present invention. Preferably, the patient is a mammal, and most preferably the mammal is a human.

An eighth aspect of the present invention provides a process for the preparation of an enantiomerically pure analogue of (R)-1-aminoindan (2) comprising the formation of a diastereomeric salt of the racemic analogue with 2,3,4,6-di-O-isopropylidene-2-keto -L-gulonic acid.

A ninth aspect of the present invention provides a process for the preparation of enantiomerically pure (R)-2-methylamino-1-phenyl-propane comprising the formation of a diastereomeric salt of 2-methylamino-1-phenyl-propane with 2,3,4,6-di-O -isopropylidene-2-keto-L-gulonic acid. Preferably the 2-methylamino-1-phenyl -propane used is racemic. (R)-2-methylamino-1-phenyl-propane is a precursor to selegiline.

Any preferred embodiment or feature of the process of the first aspect of the present invention is equally a preferred embodiment or feature of the process of the eighth and the ninth aspect of the present invention.

DETAILED DESCRIPTION OF THE INVENTION

The present invention provides a simple, convenient and inexpensive method for the preparation of enantiomerically pure (R)-1-aminoindan (2), which can be readily converted to rasagiline (1) and its pharmaceutically acceptable salts, such as rasagiline mesylate (see, for example, methods reported in U.S. Pat. No. 5,457,133). The products obtained from the process of the present invention are surprisingly very pure without the need for cumbersome purification techniques.

The advantages of the present invention are the use of inexpensive, non-hazardous synthetic agents, and simple and convenient process conditions which afford the resultant products with very high chemical and optical purity.

In a preferred embodiment of the present invention there is provided a process for the preparation of (R)-1-aminoindan (2) by resolution of racemic 1-aminoindan using 2,3,4,6-di-O-isopropylidene-2-keto-L-gulonic acid. This process gives (R)-1-aminoindan (2) in very high yield and optical purity.

The 2,3,4,6-di-O-isopropylidene-2-keto-L-gulonic acid is preferably used in the form of its monohydrate.

A particularly preferred embodiment of the present invention is a process for the preparation of (R)-1-aminoindan (2) comprising the steps of:
(a) providing a mixture of racemic 1-aminoindan and an alcohol;
(b) adding a mixture of 2,3,4,6-di-O-isopropylidene-2-keto-L-gulonic acid monohydrate in the same alcohol, optionally mixed with water;
(c) filtering the salt;
(d) optionally heating the salt in an alcohol and water mixture, cooling and isolating the salt;
(e) stirring the salt in a mixture of an inorganic base and water;
(f) extraction with a water immiscible solvent; and
(g) distillation to remove the solvent.

In step (b), instead of adding a mixture of 2,3,4,6-di-O-isopropylidene-2-keto-L -gulonic acid monohydrate, an alcohol and optionally water to a mixture of racemic 1-aminoindan and an alcohol, a mixture of racemic 1-aminoindan and an alcohol can be added to a mixture of 2,3,4,6-di-O-isopropylidene-2-keto-L-gulonic acid monohydrate, an alcohol and optionally water.

Preferably the mixture of 2,3,4,6-di-O-isopropylidene-2-keto-L-gulonic acid monohydrate, an alcohol and optionally water used in step (b) is a solution.

Preferably, the alcohol solvent is selected from the group comprising methanol, ethanol, n-propanol, isopropanol, n-butanol, isobutanol, tert-butanol and mixtures thereof. Most preferably, the alcohol is methanol.

Preferably, in step (d), the alcohol and water mixture is heated at reflux. Preferably, the alcohol to water ratio is between from 1:0.75 to 1:1.5.

Preferably, in step (d), the mixture is cooled to 10-25° C.

Preferably, in step (e), the salt is stirred with an aqueous solution of an inorganic base selected from the group comprising sodium carbonate, sodium bicarbonate, sodium hydroxide, potassium carbonate, potassium hydroxide and ammonium hydroxide.

The reagents and solvents described above are merely illustrative of the present invention and the reactions are not limited by these reagents and solvents. Any suitable alternatives can be used as outlined above.

The (R)-1-aminoindan (2) can be readily converted to rasagiline (1) and its pharmaceutically acceptable salts including acid addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulfuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulfonic acids (for example, methanesulfonic, trifluoromethanesulfonic, ethanesulfonic, 2-hydroxyethanesulfonic, benzenesulfonic, toluene-p-sulfonic, naphthalene-2-sulfonic or camphorsulfonic acid) or amino acids (for example, ornithinic, glutamic or aspartic acid). A preferred pharmaceutically acceptable salt of rasagiline (1) is the methanesulfonic acid addition salt, also called rasagiline mesylate (see, for example, methods reported in U.S. Pat. No. 5,457,133). The conversion of rasagiline (1) to rasagiline mesylate can be achieved by following well-established and reported routes of salt formation.

Preferably, the (R)-1-aminoindan (2), rasagiline (1) and rasagiline mesylate are obtained in a yield of 70% or more, preferably 80% or more, preferably 90% or more, preferably 95% or more.

Preferably, the (R)-1-aminoindan (2), rasagiline (1) and rasagiline mesylate are obtained on a commercial scale, preferably in batches of 1 kg or more, 10 kg or more, 100 kg or more, 500 kg or more, or 1000 kg or more.

Preferably, the (R)-1-aminoindan (2), rasagiline (1) and rasagiline mesylate obtained are enantiomerically pure.

Preferably, the (R)-1-aminoindan (2), rasagiline (1) and rasagiline mesylate are obtained substantially free of chemical impurities.

The process of the present invention can be easily adapted for the preparation of amines, which are analogous to rasagiline (1) or its precursor (R)-1-aminoindan (2), such as for example selegiline and its precursor (R)-2-methylamino-1-phenyl-propane. Thus the present invention also provides a process for the preparation of (R)-2-methylamino-1-phenyl-propane comprising the formation of a diastereomeric salt of 2-methylamino-1-phenyl-propane with 2,3,4,6-di-O-isopropylidene-2-keto-L-gulonic acid.

The pharmaceutical composition according to the sixth aspect of the present invention can be a solution or suspension form, but is preferably a solid oral dosage form. Preferred dosage forms in accordance with the invention include tablets, capsules and the like which, optionally, may be coated if desired. Tablets can be prepared by conventional techniques, including direct compression, wet granulation and dry granulation. Capsules are generally formed from a gelatin material and can include a conventionally prepared granulate of excipients in accordance with the invention.

The pharmaceutical composition according to the present invention typically comprises one or more conventional pharmaceutically acceptable excipient(s) selected from the group comprising a filler, a binder, a disintegrant, a lubricant, and optionally further comprises at least one excipient selected from colouring agents, adsorbents, surfactants, film-formers and plasticizers.

As described above, the pharmaceutical composition of the invention typically comprises one or more fillers such as microcrystalline cellulose, lactose, sugars, starches, modified starches, mannitol, sorbitol and other polyols, dextrin, dextran or maltodextrin; one or more binders such as lactose, starches, modified starch, maize starch, dextrin, dextran, maltodextrin, microcrystalline cellulose, sugars, polyethylene glycols, hydroxypropyl cellulose, hydroxypropyl methyl cellulose, ethyl cellulose, hydroxyethyl cellulose, methyl cellulose, carboxymethyl cellulose, gelatine, acacia gum, tragacanth, polyvinylpyrrolidone or crospovidone; one or more disintegrating agents such as croscarmellose sodium, cross-linked polyvinylpyrrolidone, crospovidone, cross-linked carboxymethyl starch, starches, microcrystalline cellulose or polyacrylin potassium; one or more different glidants or lubricants such as magnesium stearate, calcium stearate, zinc stearate, calcium behenate, sodium stearyl fumarate, talc, magnesium trisilicate, stearic acid, palmitic acid, carnauba wax or silicon dioxide.

If required, the pharmaceutical composition of the present invention may also include surfactants and other conventional excipients.

If the solid pharmaceutical formulation is in the form of coated tablets, the coating may be prepared from at least one film-former such as hydroxypropyl methyl cellulose, hydroxypropyl cellulose or methacrylate polymers which optionally may contain at least one plasticizer such as polyethylene glycols, dibutyl sebacate, triethyl citrate, and other pharmaceutical auxiliary substances conventional for film coatings, such as pigments, fillers and others.

The following paragraphs enumerated consecutively from 1 through 32 provide for various aspects of the present invention. In one embodiment, the present invention provides:

1. A process for the preparation of enantiomerically pure (R)-1-aminoindan (2) comprising the formation of a diastereomeric salt of 1-aminoindan with 2,3,4,6-di-O-isopropylidene-2-keto-L-gulonic acid.
2. A process according to paragraph 1, wherein the salt formation takes place in an organic solvent or a mixture of an organic solvent and water.
3. A process according to paragraph 2, wherein the organic solvent is a $C_1$-$C_6$ alcohol.
4. A process according to paragraph 3, wherein the organic solvent is selected from the group comprising methanol, ethanol, n-propanol, isopropanol, n-butanol, isobutanol, tert-butanol and mixtures thereof.
5. A process according to paragraph 4, wherein the organic solvent is methanol or a mixture of methanol and water.
6. A process according to any preceding paragraph, wherein the diastereomeric salt formed is recrystallised.
7. A process according to paragraph 6, wherein the diastereomeric salt formed is recrystallised from an organic solvent or water or a mixture thereof.
8. A process according to paragraph 7, wherein the diastereomeric salt formed is recrystallised from a mixture of an organic solvent and water.
9. A process according to paragraph 7 or 8, wherein the organic solvent is a $C_1$-$C_6$ alcohol.
10. A process according to paragraph 9, wherein the organic solvent is selected from the group comprising methanol, ethanol, n-propanol, isopropanol, n-butanol, isobutanol, tert-butanol and mixtures thereof.
11. A process according to paragraph 10, wherein the diastereomeric salt formed is recrystallised from a mixture of methanol and water.
12. A process according to paragraph 11, wherein the methanol to water ratio is between from about 1:0.75 to 1:1.5.

13. A process according to any preceding paragraph, wherein the (R)-1-aminoindan (2) formed is converted to rasagiline (1) or a pharmaceutically acceptable salt thereof.
14. A process according to paragraph 13, wherein the pharmaceutically acceptable salt is a mesylate salt.
15. Rasagiline (1) or a pharmaceutically acceptable salt thereof, when prepared by a process according to paragraph 13.
16. Rasagiline mesylate, when prepared by a process according to paragraph 14.
17. Enantiomerically pure rasagiline (1) or an enantiomerically pure pharmaceutically acceptable salt of rasagiline (1), when prepared by a process according to paragraph 13.
18. Enantiomerically pure rasagiline mesylate, when prepared by a process according to paragraph 14.
19. Enantiomerically pure rasagiline (1) or an enantiomerically pure pharmaceutically acceptable salt of rasagiline (1).
20. Enantiomerically pure rasagiline mesylate.
21. Rasagiline (1) or a pharmaceutically acceptable salt thereof substantially free of chemical impurities.
22. Rasagiline mesylate substantially free of chemical impurities.
23. Rasagiline (1) or a pharmaceutically acceptable salt thereof according to paragraph 15, 17, 19 or 21, for treating or preventing Parkinson's Disease (PD) (including as monotherapy or as adjunct therapy to levodopa), dementia, Alzheimer's Disease, depression, hyperactive syndrome, stroke, brain ischemia, neurotrauma, schizophrenia or multiple sclerosis.
24. Rasagiline mesylate according to paragraph 16, 18, 20 or 22, for treating or preventing Parkinson's Disease (PD) (including as monotherapy or as adjunct therapy to levodopa), dementia, Alzheimer's Disease, depression, hyperactive syndrome, stroke, brain ischemia, neurotrauma, schizophrenia or multiple sclerosis.
25. A pharmaceutical composition comprising the rasagiline (1) or a pharmaceutically acceptable salt thereof according to paragraph 15, 17, 19, 21 or 23.
26. A pharmaceutical composition comprising the rasagiline mesylate according to paragraph 16, 18, 20, 22 or 24.
27. A pharmaceutical composition according to paragraph 25 or 26, for the treatment or prevention of Parkinson's Disease (PD) (including as monotherapy or as adjunct therapy to levodopa), dementia, Alzheimer's Disease, depression, hyperactive syndrome, stroke, brain ischemia, neurotrauma, schizophrenia or multiple sclerosis.
28. A method of treating or preventing Parkinson's Disease (PD) (including as monotherapy or as adjunct therapy to levodopa), dementia, Alzheimer's Disease, depression, hyperactive syndrome, stroke, brain ischemia, neurotrauma, schizophrenia or multiple sclerosis, comprising administering to a patient in need thereof a therapeutically or prophylactically effective amount of the rasagiline (1) or a pharmaceutically acceptable salt thereof according to paragraph 15, 17, 19, 21 or 23, or a therapeutically or prophylactically effective amount of the rasagiline mesylate according to paragraph 16, 18, 20, 22 or 24, or a therapeutically or prophylactically effective amount of the pharmaceutical composition according to paragraph 25, 26 or 27.
29. A method according to paragraph 28, wherein the patient is a mammal.
30. A method according to paragraph 29, wherein the mammal is a human.
31. A process for the preparation of an enantiomerically pure analogue of (R)-1-aminoindan (2) comprising the formation of a diastereomeric salt of the racemic analogue with 2,3,4,6-di-O-isopropylidene-2-keto-L-gulonic acid.
32. A process for the preparation of enantiomerically pure (R)-2-methylamino-1-phenyl-propane comprising the formation of a diastereomeric salt of 2-methylamino-1-phenyl-propane with 2,3,4,6-di-O-isopropylidene-2-keto-L-gulonic acid.

Experimental details of preferred examples of the invention are given below.

EXAMPLES

Example 1

(R)-1-Aminoindan (2)

Racemic 1-aminoindan (1 equivalent) was dissolved in methanol (3 vol) and a solution of 2,3,4,6-di-O-isopropylidene-2-keto-L-gulonic acid monohydrate (1 equivalent) in methanol (3 vol) was added. The precipitated solid was filtered, washed with methanol (1 vol) and dried under vacuum at 40° C. The product was obtained as a white solid.

The above salt was dissolved in methanol (20 vol) and water (15 vol) at reflux and cooled to 20-25° C. before filtration. The product was dried under vacuum at 40° C. to obtain a white solid.

Salt breaking was accomplished by adding the above salt (1 equivalent) to a 10% aqueous solution of sodium carbonate (10 vol), stirring for 30 minutes and extracting the product with DCM (3×5 vol). The DCM layer with washed with water (3×5 vol) and the DCM removed under vacuum at 40° C. The product was obtained as light green coloured oil.

Yield=40%
Chemical purity=99.95% (measured by HPLC)
Optical purity=96.5% (measured by chiral HPLC)

Example 2

(R)-1-Aminoindan (2)

Racemic 1-aminoindan (1 equivalent) was dissolved in methanol (7 vol) and heated to reflux. A solution of 2,3,4,6-di-O-isopropylidene-2-keto-L-gulonic acid monohydrate (0.75 equivalent) in methanol (7 vol) was prepared and water (7 vol) was added. The solution of the gulonic acid was then added to the reaction mixture at reflux temperature. The mixture was heated at reflux for 1 hour and allowed to cool to 25-30° C. slowly under stirring. The precipitated solid was filtered, washed with methanol (2 vol) and dried under vacuum at 40° C. The product was obtained as a white solid.

Salt breaking was accomplished by adding the above salt (1 equivalent) to a solution of sodium hydroxide (2 equivalent) in water (6 vol) at 25-30° C., stirring for 1 hour and extracting the product with DCM (3×3 vol). The DCM layer was washed with water (3 vol) and the DCM removed under vacuum at 40° C. The product was obtained as light green coloured oil.

Yield=41-42%
Chemical purity=99.96% (measured by HPLC)
Optical purity=96.8% (measured by chiral HPLC)

The difficulties encountered in the prior art when preparing (R)-1-aminoindan (2) and rasagiline (1) have been successfully overcome by the process of the present invention.

No traces of any chemical impurities were observed by HPLC in the (R)-1-aminoindan (2) or rasagiline (1), when prepared following the process of the present invention.

It will be understood that the present invention has been described above by way of example only. The examples are not intended to limit the scope of the invention. Various modifications and embodiments can be made without departing from the scope and spirit of the invention, which is defined by the following claims only.

What is claimed is:

1. A process for the preparation of enantiomerically pure (R)-2-methylamino-1-phenyl-propane comprising the formation of a diastereomeric salt of 2-methylamino-1-phenyl-propane with 2,3,4,6-di-O-isopropylidene-2-keto-L-gulonic acid.

2. A process according to claim 1, wherein the salt formation takes place in an organic solvent or a mixture of an organic solvent and water.

3. A process according to claim 2, wherein the organic solvent is a $C_1$-$C_6$ alcohol.

4. A process according to claim 3, wherein the organic solvent is selected from the group comprising methanol, ethanol, n-propanol, isopropanol, n-butanol, isobutanol, tert-butanol and mixtures thereof.

5. A process according to claim 4, wherein the organic solvent is methanol or a mixture of methanol and water.

6. A process according to claim 1, wherein the diastereomeric salt formed is recrystallised.

7. A process according to claim 6, wherein the diastereomeric salt formed is recrystallised from an organic solvent or water or a mixture thereof.

8. A process according to claim 7, wherein the diastereomeric salt formed is recrystallised from a mixture of an organic solvent and water.

9. A process according to claim 7, wherein the organic solvent is a $C_1$-$C_6$ alcohol.

10. A process according to claim 9, wherein the organic solvent is selected from the group comprising methanol, ethanol, n-propanol, isopropanol, n-butanol, isobutanol, tert-butanol and mixtures thereof.

11. A process according to claim 10, wherein the diastereomeric salt formed is recrystallised from a mixture of methanol and water.

12. A process according to claim 11, wherein the methanol to water ratio is between from about 1:0.75 to 1:1.5.

13. A process according to claim 1, wherein the (R)-2-methylamino-1-phenyl-propane formed is converted to selegiline or a pharmaceutically acceptable salt thereof.

14. A process according to claim 13, wherein the pharmaceutically acceptable salt is a hydrochloride salt.

* * * * *